(12) United States Patent
Delisle et al.

(10) Patent No.: US 11,013,931 B2
(45) Date of Patent: May 25, 2021

(54) MODULAR MEDICAL SYSTEM FOR PATIENT MONITORING AND ELECTRICAL THERAPY DELIVERY

(71) Applicant: KONINKLIJKE PHILIPS N.V., Eindhoven (NL)

(72) Inventors: Norman Maurice Delisle, Manchester, MA (US); Patrick Guiney, Concord, MA (US); Harald Greiner, Nufringen (DE)

(73) Assignee: Koninklijke Philips N.V., Eindhoven (NL)

( * ) Notice: Subject to any disclaimer, the term of this patent is extended or adjusted under 35 U.S.C. 154(b) by 122 days.

(21) Appl. No.: 15/555,088

(22) PCT Filed: Mar. 2, 2016

(86) PCT No.: PCT/EP2016/054399
§ 371 (c)(1),
(2) Date: Sep. 1, 2017

(87) PCT Pub. No.: WO2016/139234
PCT Pub. Date: Sep. 9, 2016

(65) Prior Publication Data
US 2018/0036544 A1 Feb. 8, 2018

Related U.S. Application Data

(60) Provisional application No. 62/127,473, filed on Mar. 3, 2015.

(51) Int. Cl.
*A61N 1/39* (2006.01)
*A61N 1/04* (2006.01)
(Continued)

(52) U.S. Cl.
CPC ........ *A61N 1/3968* (2013.01); *A61B 5/02055* (2013.01); *A61N 1/046* (2013.01);
(Continued)

(58) Field of Classification Search
CPC ................ A61B 5/0402; A61B 5/0452; A61B 2560/0456; A61N 1/37; A61N 1/39; A61N 1/3925
See application file for complete search history.

(56) References Cited

U.S. PATENT DOCUMENTS 5,105,821 A   4/1992 Reyes
5,640,953 A * 6/1997 Bishop ................ G06F 19/3418
                                                    600/300

(Continued)

OTHER PUBLICATIONS

Anonymous:"IntelliVue MX800 Patient Monitor", Philips, 2010. https://www.usa.philips.com/healthcare/product/HC865240/intellivue-mx800-bedside-patient-monitor.

(Continued)

*Primary Examiner* — Michael J D Abreu

(57) ABSTRACT

A modular medical system employing a bedside patient monitor (20), a portable patient monitor (40), a monitor docking station (50), a therapy applicator (30) and a therapy docking station (60). In operation, the portable patient monitor (40) is docked to the bedside patient via the monitor docking station (50) whereby the bedside patient monitor (20) and the portable patient monitor (40) measure patient parameters (e.g., ECG, Sp O2, pulse rate, NIBP, Et CO2, etc.) upon the portable patient monitor (40) being coupled to a patient. Alternatively, the portable patient monitor (40) is docked to the therapy applicator (30) via the therapy docking station (60) whereby the therapy applicator (30) conditionally delivers the electrical therapy (e.g., defibrillation shock, synchronized conversion, transcutaneous pacing, etc.) to the patient upon the portable patient monitor (40) being coupled to the patient.

15 Claims, 5 Drawing Sheets

(51) Int. Cl.
*A61B 5/0205* (2006.01)
*A61B 5/318* (2021.01)
*A61B 5/0215* (2006.01)
*A61B 5/083* (2006.01)
*A61B 5/145* (2006.01)

(52) U.S. Cl.
CPC ......... *A61N 1/3925* (2013.01); *A61N 1/3937* (2013.01); *A61N 1/3975* (2013.01); *A61B 5/0215* (2013.01); *A61B 5/0836* (2013.01); *A61B 5/14542* (2013.01); *A61B 5/318* (2021.01); *A61B 2560/0431* (2013.01); *A61B 2560/0456* (2013.01)

(56) References Cited

U.S. PATENT DOCUMENTS

| | | | | |
|---|---|---|---|---|
| 5,682,902 | A * | 11/1997 | Herleikson | A61B 5/0452 128/901 |
| 5,685,314 | A * | 11/1997 | Geheb | G16H 40/63 600/513 |
| 6,183,417 | B1 * | 2/2001 | Geheb | G06F 19/3418 600/301 |
| 6,221,012 | B1 | 4/2001 | Maschke et al. | |
| 6,591,135 | B2 * | 7/2003 | Palmer | A61B 5/04 607/34 |
| 2003/0105403 | A1 * | 6/2003 | Istvan | A61B 5/0006 600/509 |
| 2005/0033124 | A1 | 2/2005 | Kelly et al. | |
| 2006/0094936 | A1 | 5/2006 | Russ | |
| 2006/0142808 | A1 | 6/2006 | Pearce et al. | |
| 2006/0149321 | A1 | 7/2006 | Merry et al. | |
| 2013/0245486 | A1 * | 9/2013 | Simon | A61B 5/7264 600/546 |
| 2018/0036544 | A1 | 2/2018 | Delisle et al. | |

OTHER PUBLICATIONS

Anonymous: "IntelliVue X2 Multi-Measurement Module", Philips, 2007. https://www.usa.philips.com/healthcare/product/HC865039/intellivue-mms-x2-measurement-module-monitor.

* cited by examiner

DOCKING OF PORTABLE PATIENT MONITOR-BEDSIDE PATIENT MONITOR

DOCKING OF PORTABLE PATIENT MONITOR-DEFIBRILLATOR

MODULAR MEDICAL SYSTEM FOR PATIENT MONITORING AND ELECTRICAL THERAPY DELIVERY

This application is a national stage application under 35 U.S.C. § 371 of International Application No. PCT/EP2016/054399 filed on Mar. 2, 2016 and published in the English language on Sep. 9, 2016 as International Publication No. WO2016/139234, which claims priority to U.S. Patent Application No. 62/127,473 filed on Mar. 3, 2015, the entire disclosures of which are incorporated herein by reference.

FIELD OF THE INVENTION

The present invention generally relates to modular medical systems (e.g., a module system employing a bedside patient monitor and a defibrillator/monitor). The present invention specifically relates to a portable patient monitor capable of being docked with a bedside patient monitor or a therapy applicator (e.g., a defibrillator).

BACKGROUND OF THE INVENTION

Portable defibrillator/monitors are used in hospitals and outside hospitals for emergency medical care. These devices incorporate one or more vital signs monitoring parameters such as, for example, electrocardiogram ("ECG"), pulse oximetry ("SpO2"), non-invasive blood pressure ("NIBP"), exhaled (end tidal) carbon dioxide ("EtCO2"), temperature and invasive blood pressure ("IBP"). These devices further incorporate electrical therapy delivery capabilities such as, for example, a defibrillation shock, synchronized cardioversion and transcutaneous pacing.

In a modular version of a portable defibrillator/monitor, all or part of the patient measurement capability is primarily provided by a portable patient monitor that is separable from the defibrillator for the high energy therapy delivery. The portable patient monitor is typically smaller and lighter than the defibrillator, which houses larger and heavier electrical components needed for the high energy therapy delivery. Because the portable patient monitor is small and light, the portable patient monitor can be handled easily and may be placed on a stretcher with the patient to provide continuous monitoring of the patient's vital parameters as the patient is transported.

For example, a commercially available modular defibrillator/monitor known as the corpuls[3] may be split into a monitoring unit, a patient box and a defibrillator/pacer unit. When split apart, these modules are capable of wireless communication with the patient box providing a display and user interface controls for both the monitoring unit and the defibrillator/pacer unit.

By comparison, beside patient monitors may also incorporate modular capabilities to span care environments, patient acuity levels, and clinical requirements. More particularly, a bedside patient monitor, such as, for example, the commercially available IntelliVue MX800, may support multi-measurement monitoring via a the commercially available flexible module rack (which can hold up to eight (8) measurement modules) or via multi-measurement modules such as, for example, the IntelliVue X2, which can also operate as a portable patient monitor.

As known in the art, high-acuity patients are monitored continuously as being transported to a hospital and within the hospital. For example, referring to FIG. 1, a bedside patient monitor 20 is typically mounted to a wall in a patient space 10 (e.g., an ambulance, a patient room or an operating room) adjacent a patient bed 12 and the following measurements of a high-acuity patient 11 are made by beside patient monitor 20:

(1) electrocardiogram ("ECG") with electrodes/leads 13a coupling the beside patient monitor 20 to a chest of patient 11,
(3) non-invasive blood pressure ("NIBP") with a cuff 14 coupling beside patient monitor 20 to an arm of patient 11, and
(2) pulse oximetry ("SpO2") with a fingertip sensor 15 coupling beside patient monitor 20 to a finger of patient 11.

Additional monitored parameters might include exhaled carbon dioxide ("EtCO2"), temperature and invasive blood pressure ("IBP").

When there is a need to transport the high-acuity patient to another area of the hospital or another facility (e.g., from a patient room to radiology for a CT Scan), hospital protocols frequently mandate that the patient is connected to a defibrillator for quickly delivering a shock if the patient succumbs to sudden cardiac arrest ("SCA") while being transported. For SCA, immediate treatment increases the likelihood of survival and neurological recovery.

As shown in FIG. 1, bedside patient monitors are typically mounted to the wall of the patient's room as stated earlier. Therefore, defibrillators used for patient transport typically incorporate their own patient monitoring capabilities. Thus, to transport a high-acuity patient, the leads attached from the bedside patient monitor to the patient must be detached, and a new set of leads must be connected from the high-acuity patient to the defibrillator. At the destination (which might be returning to the original patient room), the leads from the defibrillator to the patient must be detached and a new set of leads must be attached from the patient to a bedside patient monitor unit.

For example, as shown in FIG. 1, bedside patient monitor 20 is mounted to the wall in patient space 10, and a defibrillator 30 incorporates its own patient monitoring capability for patient transport purposes. When preparing high-acuity patient 11 for transportation to another patient space (i.e., a destination), electrode/leads 13a attached from the bedside patient monitor 20 to patient 11 must be detached, and a different set of electrode/leads 13b must be connected from the patient 11 to defibrillator 30 whereby defibrillator 30 may conditionally deliver an electric therapy to patient 11 via pads/paddles 31. At the destination, electrode/leads 13b from defibrillator 20 to the patient 11 must be detached and a new set of electrode/leads must be attached from patient 11 to another bedside patient monitor or beside patient monitor 20 if returning to patient space 10). Additionally, when preparing patient 11 for transportation, a new cuff and/or a fingertip sensor may be needed to replace cuff 14 and/or sensor 15.

SUMMARY OF THE INVENTION

The present invention advances the prior art by providing a selective docking of a complete stand-alone portable patient monitor to a beside patient monitor or to a therapy applicator (e.g., a defibrillator).

For example, as shown in FIG. 2, when patient 11 is resting on patient bed 12 within patient space 10, a portable patient monitor 40 (e.g., IntelliVue X2) is docked with bedside patient monitor 20 (e.g., IntelliVue MX800) via a monitoring docking station 50 whereby bedside patient monitor 20 and portable patient monitor 40 execute various parameter measurements (e.g., ECG, NIBP and SpO2) of patient 11 from electrode/leads 13c, cuff 14 and sensor 15 coupling portable patient monitor 40 to patient 11. When preparing patient 11 for transportation to another patient space, electrode/leads 13c are not detached from bedside patient monitor 20 to patient 11 as known in the art. Conversely, electrode/leads 13c as well as cuff 14 and sensor 15 remain attached to patient 11 as portable patient monitor 40 is undocked from beside patient monitor 20 and docked to defibrillator 30 via a therapy docking station 60 whereby defibrillator 30 may conditionally deliver an electric therapy to patient 11 via pads/paddles 31. At the destination, electrode/leads 13c as well as cuff 14 and sensor 15 remain attached to patient 11 as portable patient monitor 40 may be undocked from docking station 60 and docked to a bedside patient monitor via a monitoring docking station (e.g., a re-docking of portable patient monitor 40 to bedside patient monitor 20 upon a return to patient space 10).

This new and unique docking scheme may be implemented in many forms for modular medical systems including, but not limited to, commercially available modular medical systems and for newly developed or in development modular medical systems One form of the present invention is a modular medical system employing a bedside patient monitor, a portable patient monitor, a monitor docking stations, a therapy applicator and a therapy docking station. In operation, the portable patient monitor is docked to the bedside patient via the monitor docking station whereby the bedside patient monitor and the portable patient monitor measure patient parameters (e.g., ECG, SpO2, pulse rate, NIBP, EtCO2, etc.) upon the portable patient monitor being coupled to a patient. Alternatively, the portable patient monitor is docked to the therapy applicator via the therapy docking station whereby the therapy applicator conditionally delivers the electrical therapy (e.g., defibrillation shock, synchronized conversion, transcutaneous pacing, etc.) to the patient upon the portable patient monitor being coupled to the patient.

For purposes of the present invention, terms of the art including, but not limited to, "modular medical system", "bedside patient monitor", "portable patient monitor", "docking station", "patient parameters" and "electrical therapy" are to be broadly interpreted as known in the art of the present invention and exemplary described herein.

For purposes of the present invention, the term "therapy applicator" broadly encompasses medical devices for delivering an electrical therapy to a patient including, but not limited to, a defibrillation shock, a synchronized conversion and transcutaneous pacing.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

DETAILED DESCRIPTION OF THE PREFERRED EMBODIMENTS

Figure 3:
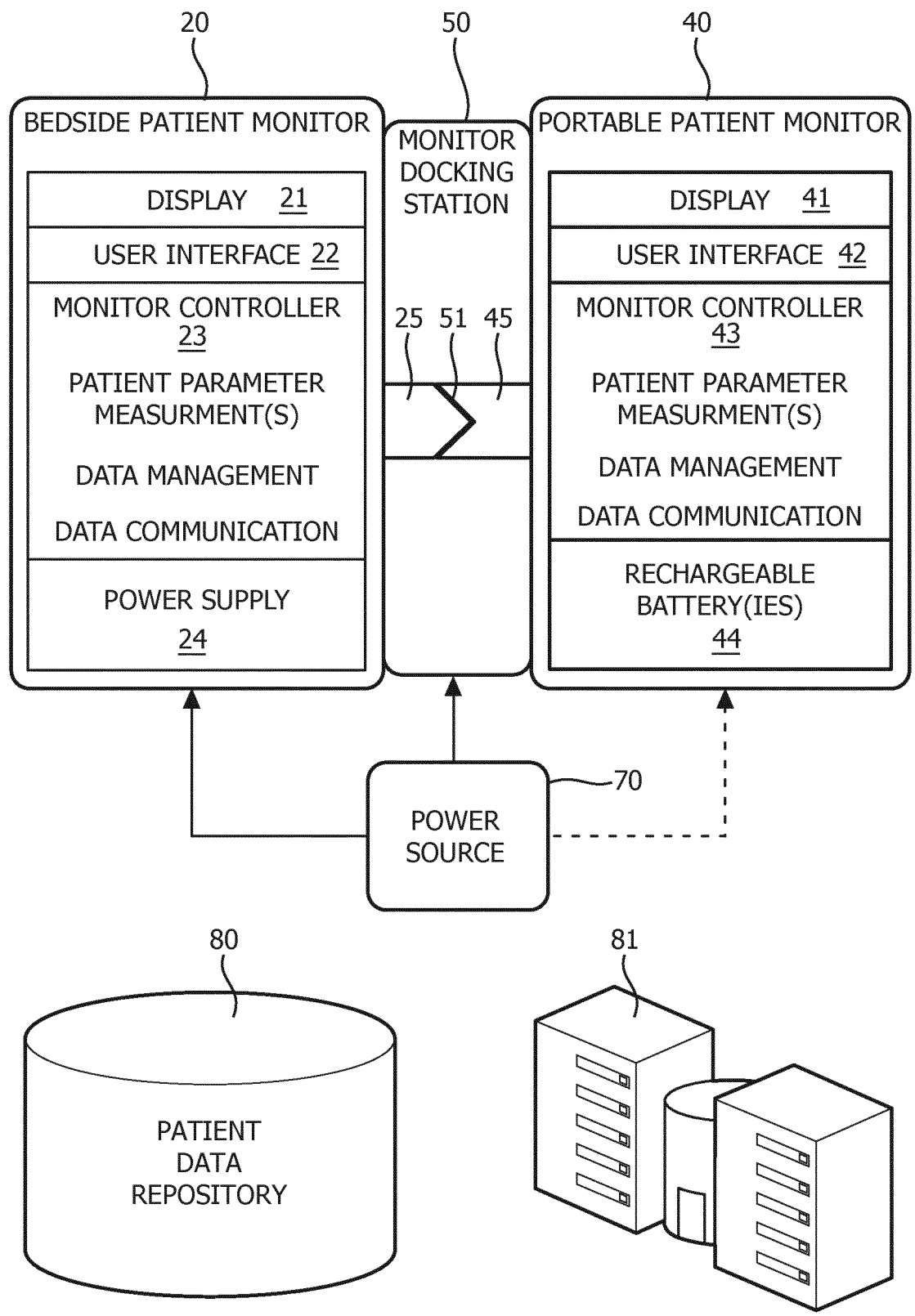
FIG. 3 illustrates exemplary embodiments of a portable patient monitor and a beside patient monitor in accordance with the inventive principles of the present invention.
Figure 4:
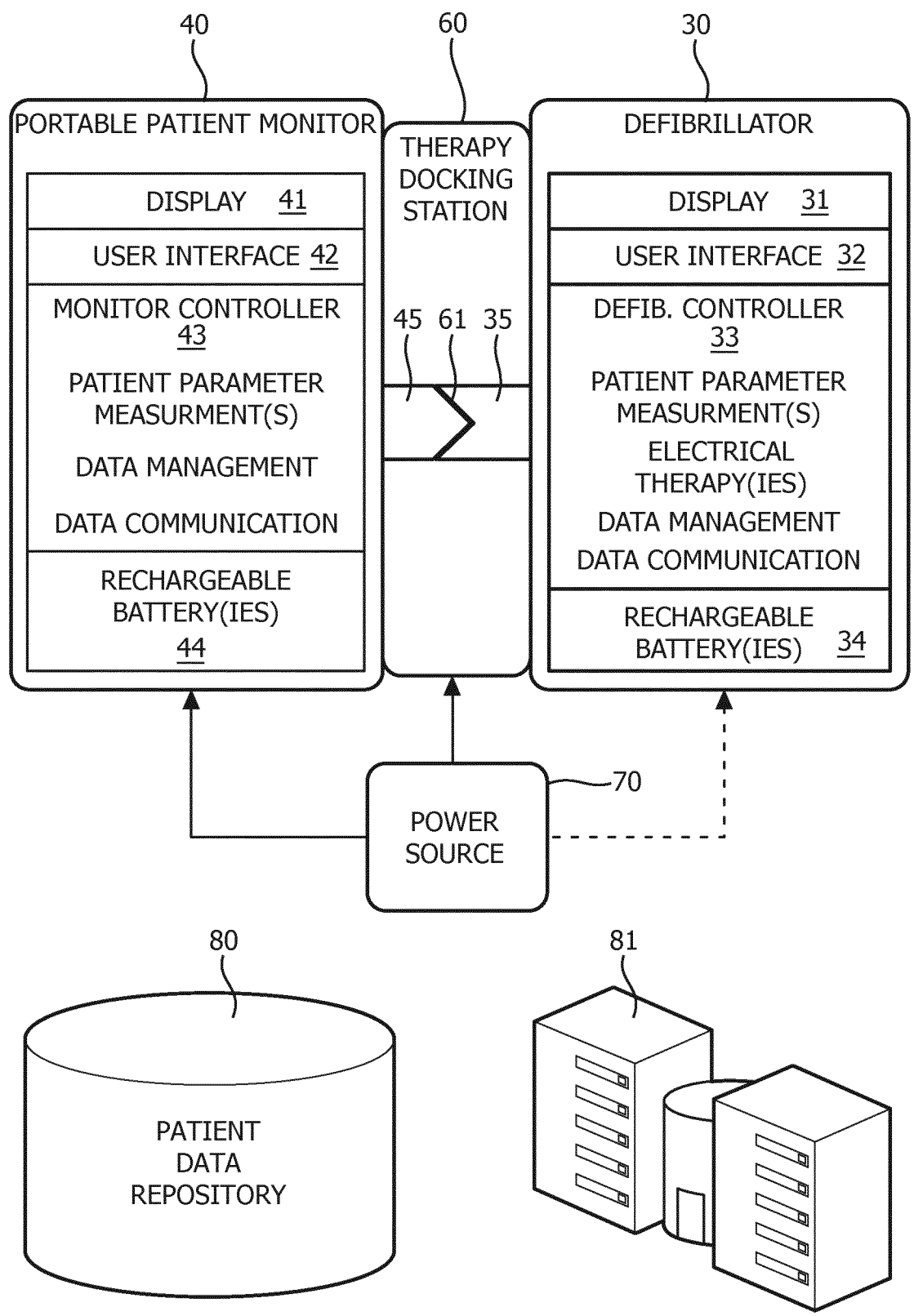
FIG. 4 illustrates exemplary embodiments of a portable patient monitor and a therapy applicator in accordance with the inventive principles of the present invention.

To facilitate an understanding of the present invention, exemplary embodiments of the present invention will be provided herein directed to a docking of portable patient monitor 40 to bedside patient monitor 20 (FIG. 3) and a docking of portable patient monitor 40 to a therapy applicator in the form a defibrillator 30 (FIG. 4). Nonetheless, those having ordinary skill in the art will appreciate who to make and use additional embodiments of the present invention in accordance with the inventive principle of the present invention as exemplarily described herein.

For purposes of the present invention, terms of the art including, but not limited to, "display", "user interface", "power supply", "batteries", "power source" and "patient data repository" are to be broadly interpreted as known in the art of the present invention and exemplary described herein.

For purposes of the present invention, the term "controller" broadly encompasses all structural configurations of an application specific main board or an application specific integrated circuit housed within or linked to a medical device for controlling an application of various inventive principles of the present invention as subsequently described herein. The structural configuration of the controller may include, but is not limited to, processor(s), computer-usable/computer readable storage medium(s), an operating system, executable software/firmware, peripheral device controller(s), slot(s) and port(s).

By the inventive principles of the present invention, FIG. 3 illustrates a docking of portable patient monitor 40 to bedside patient monitor 20 via monitor docking station 50.

Specifically, beside patient monitor 20 incorporates:
(1) a display 21 for textually and/or graphically showing patient parameter measurement(s);
(2) an user interface 22 (e.g., buttons and/or touchscreen) for selectively controlling the execution and/or display of the patient parameter measurement(s);
(3) a monitor controller 23 for automatically and/or user control measurement(s) of
   (a) patient parameter(s) (e.g., ECG, SpO2, NIBP, EtCO2, temperature and/or IBP),
   (b) data management (e.g., event recordings and transmissions), and
   (c) wired/wireless data communication with portable patient monitor 40 and a patient data repository 80; and
(4) a power supply 24 powered by a power source 70.
Portable patient monitor 40 incorporates:
(1) a display 41 for textually and/or graphically showing patient parameter measurement(s);

(2) an user interface 42 (e.g., buttons and/or touchscreen) for selectively controlling the execution and/or display of the patient parameter measurement(s);

(3) a monitor controller 43 for automatically and/or user control measurement(s) of
  (a) patient parameter(s) (e.g., ECG, SpO2, NIBP, EtCO2, temperature and/or IBP),
  (b) data management (e.g., event recordings and transmissions), and
  (c) wired/wireless data communication with bedside patient monitor 20, patient data repository 80 and/or a monitoring center 81; and (4) rechargeable battery(ies) 44 rechargeable by a power source 70.

Monitors 20 and 40 further incorporate docking interfaces 25 and 45, and monitor docking station 50 establishes a connection 61 between docking interfaces 25 and 45 to facilitate:

(1) a secure coupling of monitors 20 and 40 via a mechanical coupler (not shown) (e.g., a quick-connect/release latch);

(2) a data transfer between monitors 20 and 40 (e.g., a network, serial and/or parallel galvanic connection) (Alternatively, wireless communications such as Wi-Fi or Bluetooth may be utilized); and (3) an electrical powering of monitor 40 as needed (e.g., a galvanic connection or inductive coupling).

In practice, (1) the patient parameter measurements by bedside patient monitor 20 may be inclusive or exclusive of some or all of the patient parameter measurements by portable patient monitor 40;

(2) portable patient monitor 40 may be capable of being docked with other medical device modules via docking station 50 (e.g., imaging devices, diagnostic ECG devices, fetal monitors, etc.);

(3) display 41 of portable patient monitor 40 may be hidden when docked with bedside patient monitor 20 whereby all of patient parameter measurement(s) by portable patient monitor 40 is displayed on bedside patient monitor 20;

(4) display 41 of portable patient monitor 40 may be visible when docked with bedside patient monitor 20 whereby portable patient monitor 40 displays the patient parameter measurement(s) by portable patient monitor 40;

(5) display 41 of portable patient monitor 40 may be visible when docked with bedside patient monitor 20 whereby bedside patient monitor 20 and portable patient monitor 40 collectively or divisibly displays the patient parameter measurement(s) by portable patient monitor 40;

(6) user interface 42 of portable patient monitor 40 may be hidden when docked with bedside patient monitor 20 whereby user interface 22 of bedside patient monitor controls patient parameter measurements by portable patient monitor 40;

(7) user interface 42 of portable patient monitor 40 may be visible when docked with bedside patient monitor 20 whereby user interface 42 of portable patient monitor controls patient parameter measurements by portable patient monitor 40;

(8) user interface 42 of portable patient monitor 40 may be visible when docked with bedside patient monitor 20 whereby user interface 42 of portable patient monitor controls part or all of the patient parameter measurements by bedside patient monitor 20; and (9) monitor docking station 50 may be a stand-alone docking station, incorporated within beside patient monitor 20 or portable patient monitor 40, or integrated with therapy docking station 60 (FIG. 4).

By further inventive principles of the present invention, FIG. 4 illustrates a docking of portable patient monitor 40 to defibrillator 30 via therapy docking station 60.

Specifically, defibrillator 30 incorporates:

(1) a display 31 for textually and/or graphically showing alarm and/or therapy delivery status, (2) an user interface 32 for selectively controlling an execution and/or the display of the electrical therapy(ies), (3) a therapy controller 33 for automatically and/or user control execution of
  (a) the electrical therapy(ies) (e.g., a defibrillation shock, a synchronized cardioversion and a transcutaneous pacing,
  (b) patient parameter measurement(s) (e.g., ECG, SpO2, NIBP, EtCO2, temperature and/or IBP),
  (c) data management (e.g., event recordings and transmissions), and
  (d) wired/wireless data communication with portable patient monitor 40, patient data repository 80 and/or a monitoring center 81; and (4) rechargeable battery(ies) 34 rechargeable by power source 70.

Defibrillator 30 and monitor 40 further incorporate docking interfaces 35 and 45, and therapy docking station 60 establishes a connection 61 between docking interfaces 35 and 45 to facilitate:

(1) a secure coupling of defibrillator 30 and monitor 40 via a mechanical coupler (not shown) (e.g., a quick-connect/release latch);

(2) a data transfer between defibrillator 30 and monitor 40 (e.g., a network, serial and/or parallel galvanic connection) (Alternatively, wireless communications such as Wi-Fi or Bluetooth may be utilized); and (3) an electrical powering of monitor 40 as needed (e.g., a galvanic connection or inductive coupling).

In practice, (1) the patient parameter measurements by defibrillator 30 may be inclusive or exclusive of some or all of the patient parameter measurements by portable patient monitor 40;

(2) portable patient monitor 40 again may be capable of being docked with other medical device modules via docking station 60 (e.g., imaging devices, diagnostic ECG devices, fetal monitors, etc.);

(3) display 41 of portable patient monitor 40 may be hidden when docked with defibrillator 30 whereby all of patient parameter measurement(s) by portable patient monitor 40 is displayed on defibrillator 30;

(4) display 41 of portable patient monitor 40 may be visible when docked with defibrillator 30 whereby portable patient monitor 40 displays the patient parameter measurement(s) by portable patient monitor 40;

(5) display 41 of portable patient monitor 40 may be visible when docked with defibrillator 30 whereby defibrillator 30 and portable patient monitor 40 collectively or divisibly displays the patient parameter measurement(s) by portable patient monitor 40;

(6) user interface 42 of portable patient monitor 40 may be hidden when docked with defibrillator 30 whereby user interface 32 of defibrillator 30 controls patient parameter measurements by portable patient monitor 40;

(7) user interface 42 of portable patient monitor 40 may be visible when docked with defibrillator 30 whereby user interface 42 of portable patient monitor controls patient parameter measurements by portable patient monitor 40;

(8) user interface 42 of portable patient monitor 40 may be visible when docked with bedside patient monitor 20 whereby user interface 42 of portable patient monitor controls part or all of the patient parameter measurements by defibrillator 30; and (9) therapy docking station 60 may be a stand-alone docking station, incorporated within defibrillator 30 or portable patient monitor 40, or integrated with monitor docking station 50 (FIG. 3).

Figure 1:
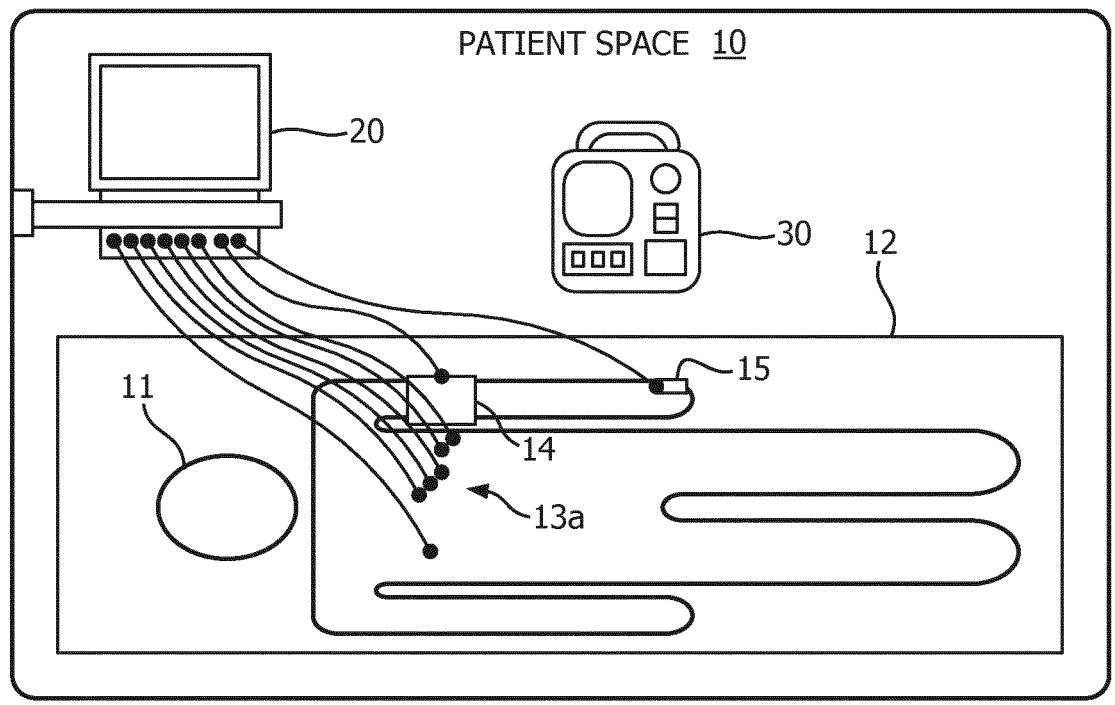
FIG. 1 illustrates exemplary couplings of bedside patient monitor-patient and defibrillator/monitor-patient in accordance with the prior art.
Figure 1:
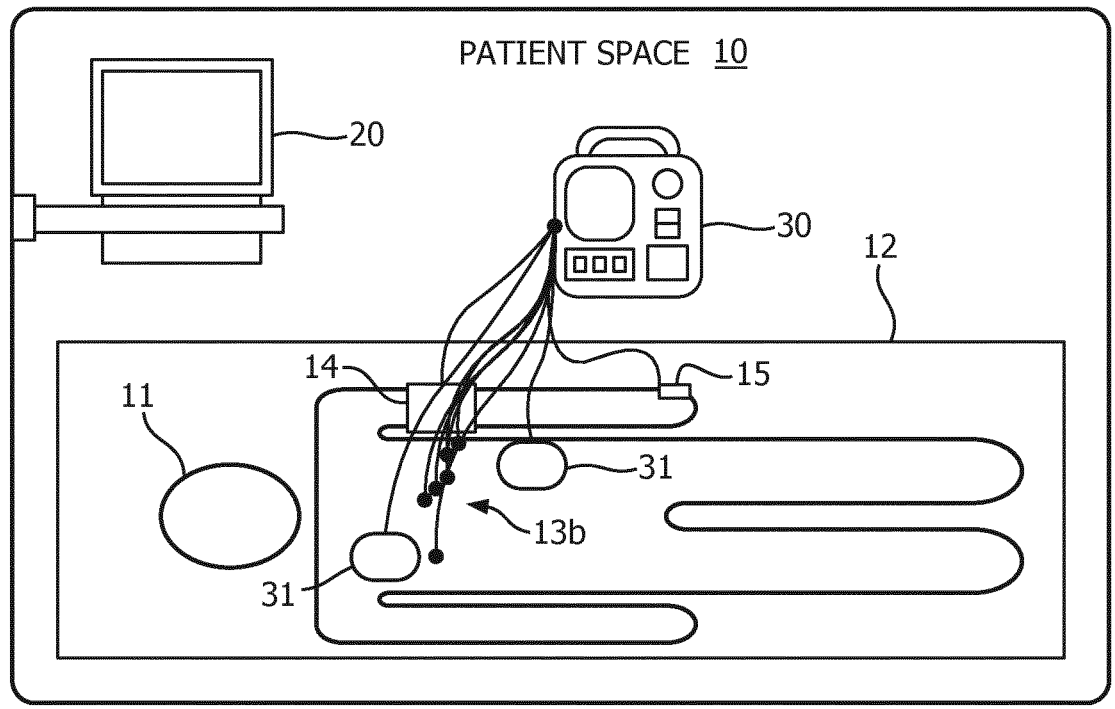
Figure 2:
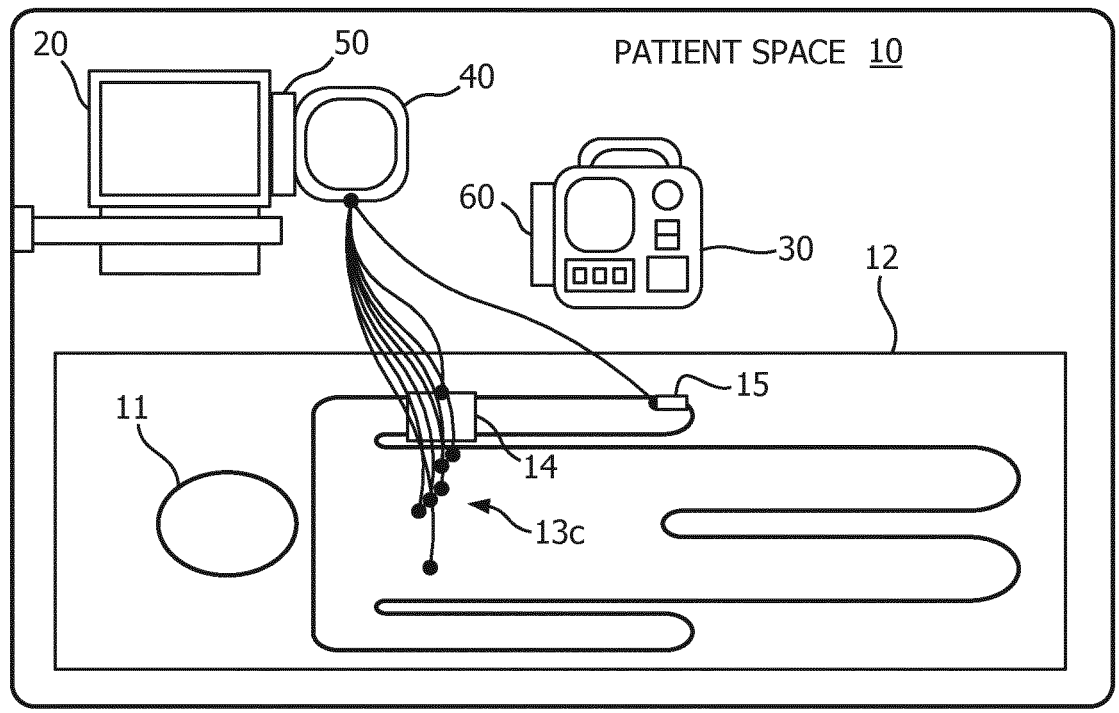
FIG. 2 illustrates exemplary docking of portable patient monitor-bedside patient monitor and portable patient monitor-defibrillator in accordance with the inventive principles of the present invention.
Figure 2:
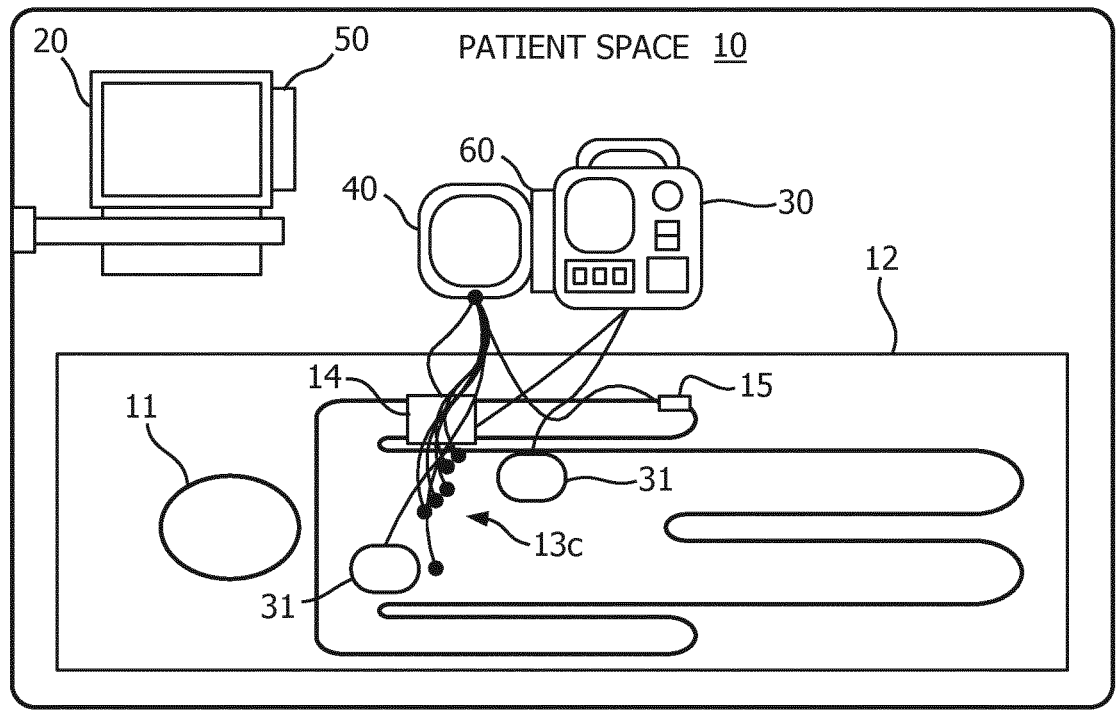

Referring to FIG. 2, in a standard operation, bedside patient monitor 20 is capable of patient parameter measurements without or without connectivity to portable patient monitor 40, and defibrillator 30 likewise is capable of delivering basic electrical therapy(ies) with or without connectivity with portable patient monitor 40.

When portable patient monitor 40 is docked with bedside patient monitor 20, monitors 20 and 40 operate as a single monitor with consistent appearance and behaviors for user interface display and controls. When the portable patient monitor 40 is undocked from bedside patient monitor 20, portable patient monitor 40 continues to operate under battery power with full patient monitoring capabilities including, but not limited to, display, user controls and data management.

Defibrillator 30 requires leads ECG monitoring to deliver a shock for synchronized cardioversion or delivery of a pace pulse due to absence of an intrinsic heartbeat (i.e. demand pacing or synchronized pacing). When portable patient monitor 40 is docked with defibrillator 30, portable patient monitor 40 includes measurement of the patient's leads ECG via 3, 4, 5, or more electrodes 13c attached to patient 11 whereby the data connection with the defibrillator 30 provides low latency to ensure appropriate timing of a synchronized shock or synchronized pacing.

Concurrently or alternatively, defibrillator 30 may include measurement of the patient's leads ECG via 3, 4, 5, or more electrodes attached to the patient 11 in an embodiment when the leads ECG are acquired by portable patient monitor 40.

Docking stations 50 and 60 provide quick attach and quick release capability, and secure attachment for robust power and data communication connections. In one embodiment, the power and data communications use a galvanic connection where the electrical energy flows via electrically conductive paths through wires and connectors (not shown). In another embodiment, the power and data communications may use wireless techniques (e.g., Wi-Fi or Bluetooth) for data communication and inductive coupling for power.

Portable patient monitor 40 manages patient data as it operates both when docked or undocked. In one embodiment, the patient data of portable patient monitor 40 may be transmitted to bedside patient monitor 20 or defibrillator 30, or directly to a patient data repository 80 (FIGS. 3 and 4) (e.g. an electronic Patient Care Reporting (ePCR) system such as Zoll RescueNet) or directly to central patient monitoring station 81 (FIGS. 3 and 4) (e.g. the Philips Intellivue Information Center). When the portable patient monitor 40 is docked, the patient data may be transferred to bedside patient monitor 20 or defibrillator 30 via the wired or wireless data communication mechanism. When portable patient monitor 40 is not docked, the patient data of portable patient monitor 40 may be transferred wirelessly to bedside patient monitor 20 or defibrillator 30. In another embodiment, the portable patient monitor 40 may temporarily store its patient data for transfer to beside patient monitor 20 or defibrillator 30 the next time it is docked.

Referring to FIGS. 3 and 4, wired communication between the modules may involve a direct electrical connection facilitated by a docking station. In practice, communication via direct electrical connection generally works well with low power, low energy modules that have inherently high signal to noise ratios, such as, for example, patient monitors 20 and 40 when docked. However, defibrillator 30 provides electrical thearpy(ies) that may generate significant noise that disturbs the direct electrical connection between defibrillator 30 and monitor 40 when docked. Furthermore, a direct electrical connection experiences wear and tear faster than other forms of communication that do not require a mechanical interface.

Alternatives to a direct electrical connection are a wireless data link and an optical data link, particularly for defibrillator 30 and monitor 40. Generally, the wireless data links use circuitry that drive antennas to transmit and receive RF energy via one or more standard protocols, and the optical data links use light sources for sensing transmitted light.

Figure 5:
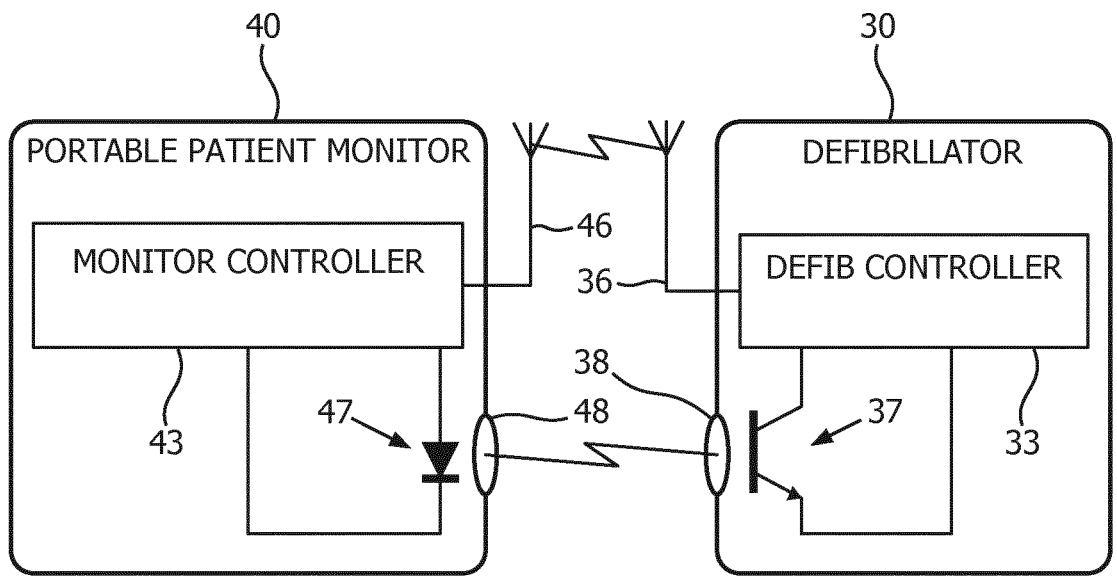
FIG. 5 illustrates a first exemplary embodiment of wireless/optical communication links between modules in accordance with the inventive principles of the present invention.
Figure 6:
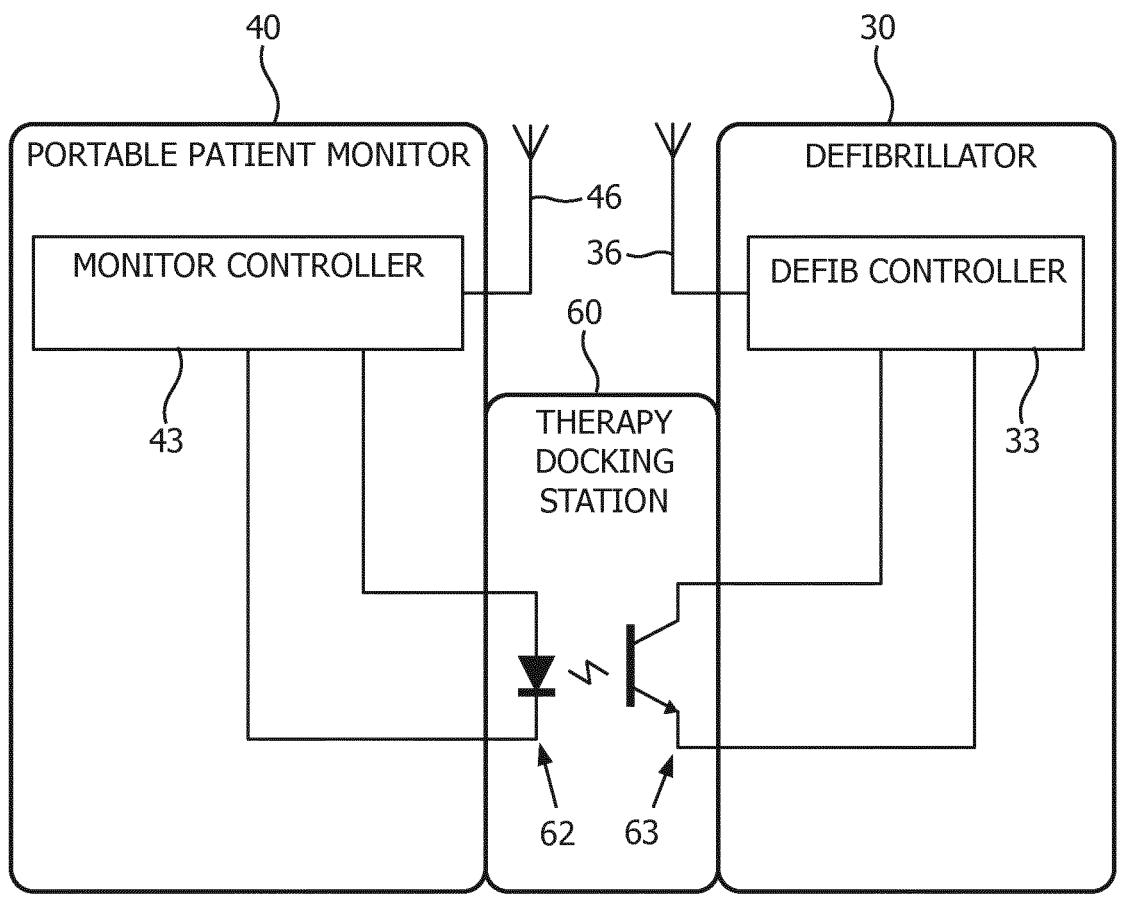
FIG. 6 illustrates a second exemplary embodiment of wireless/optical communication links between modules in accordance with the inventive principles of the present invention.

Specifically, referring to FIGS. 5 and 6, monitor 40 is shown equipped with an antenna 46 and defibrillator 30 is shown equipped with an antenna 36. In practice, controllers 33 and 43 implement one of a wide variety of wireless communication modalities and standards that allow electrically isolated communication through free space via RF energy including, but not limited to, WiFi, WiMax, Bluetooth, 3G, NFC, Zigbee, GSM and Wireless USB/Ultraband. This wireless data link is most appropriate when monitor 40 and defibrillator 30 are undocked.

Referring to FIG. 5, monitor 40 is shown equipped with a light emitting diode ("LED") 47 and defibrillator 30 is shown equipped with a photo-sensor 37. In operation, transceiver windows 48 and 38 are aligned whereby LED 47 and photo-sensor 37 are aligned whereby controller 43 energizes LED 47 to emit photons to excite photo-sensor 37 which is detected by controller 33. This optical data link is most appropriate when monitor 40 and defibrillator 30 are close, docked or undocked.

Alternatively for docking purposes, referring to FIG. 6, therapy docking station 60 may be equipped with a LED 62 and a photo-sensor 63 to establish the optical data link between monitor 40 and defibrillator 30. As with the embodiment of FIG. 5, using light to transmit data across the physical interface between monitor 40 and defibrillator 30 eliminates the need for wires, cables and connectors that may be subject to the wear and tear of micro-vibration.

In practice, the optical data links will typically be bi-directional (e.g., defibrillator 30 being equipped with a LED and monitor 40 being equipped with a photo-sensor). Furthermore, the wireless data link and optical data links illustrated in FIGS. 5 and 6 are applicable to any modular embodiment of the present invention.

Alternatively, transformers may be utilized for close data links.

Referring to FIGS. 2-6, those having ordinary skill in the art will further appreciate numerous benefits of the present invention including, but not limited to, an elimination of a need to detach and reattach patient leads and avoidance of a discontinuity in monitoring the patient when there are no leads attached.

Furthermore, as one having ordinary skill in the art will appreciate in view of the teachings provided herein, features, elements, components, etc. described in the present disclosure/specification and/or depicted in the FIGS. 2-6 may be implemented in various combinations of electronic components/circuitry, hardware, executable software and executable firmware, particularly as application modules of a controller as described herein, and provide functions which may be combined in a single element or multiple elements. For example, the functions of the various features, elements, components, etc. shown/illustrated/depicted in the FIGS. 2-6 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive modular medical systems, (which embodiments are intended to be illustrative and not limiting), it is noted that modifications and variations can be made by persons having ordinary skill in the art in light of the teachings provided herein, including the FIGS. 2-6. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. A modular medical system, comprising:
   a portable patient monitor configured to monitor first patient data or second patient data when the portable patient monitor is coupled to a patient;
   a bedside patient monitor;
   a monitor docking station configured to dock the portable patient monitor to the bedside patient monitor when the portable patient monitor is monitoring the first patient data,
      wherein the portable patient monitor is configured to transfer the monitored first patient data to the bedside patient monitor when the portable patient monitor is docked to the bedside patient monitor via the monitor docking station, and
      wherein the bedside patient monitor is configured to measure a first set of patient parameters from the first patient data when the portable patient monitor is docked to the bedside patient monitor via the monitor docking station;
   a therapy applicator; and
   a therapy docking station configured to dock the portable patient monitor to the therapy applicator when the portable patient monitor is monitoring the second patient data,
      wherein the portable patient monitor is further configured to measure the second set of patient parameters from the second patient data when the portable patient monitor is docked to the therapy applicator via the therapy docking station,
      wherein the portable patient monitor is further configured to transfer the at least one of the monitored second patient data and the measured second set of patient parameters to the therapy applicator when the portable patient monitor is docked to the therapy applicator via the therapy docking station, and
      wherein the therapy applicator is configured to deliver an electrical therapy based on at least one of the second patient data and a second set of patient parameters when the portable patient monitor is docked to the therapy applicator via the therapy docking station.

2. The modular medical system of claim 1,
   wherein the therapy applicator is further operable to measure a third set of patient parameters from the second patient data when the portable patient monitor is docked to the therapy applicator via the therapy docking station; and wherein the therapy applicator is further to deliver the electrical therapy based on at least one of the monitored second patient data, the measured second set of patient parameters, and the measured third set of patient parameters when the portable patient monitor is docked to the therapy applicator via the therapy docking station.

3. The modular medical system of claim 2, wherein the third set of patient parameters includes the second set of patient parameters.

4. The modular medical system of claim 1, wherein the monitor docking station and the therapy docking station are integrated within a single docking station.

5. The modular medical system of claim 4, wherein the single working station is incorporated within the portable patient monitor.

6. The modular medical system of claim 1, wherein the monitor docking station is incorporated within the bedside patient monitor.

7. The modular medical system of claim 1, wherein the monitor docking station is incorporated within the portable patient monitor.

8. The modular medical system of claim 1, wherein the therapy docking station is incorporated within the therapy applicator.

9. The modular medical system of claim 1, wherein the therapy docking station is incorporated within the portable patient monitor.

10. The modular medical system of claim 1, wherein the first set of patient parameters includes the second set of patient parameters.

11. The modular medical system of claim 1, wherein the monitor docking station is further configured to power the portable patient monitor.

12. The modular medical system of claim 1, wherein the therapy docking station is further configured to power the portable patient monitor.

13. The modular medical system of claim 1, wherein the bedside patient monitor and the portable patient monitor are configured to establish an optical data link responsive to the portable patient monitor being docked to the bedside patient monitor.

14. The modular medical system of claim 1, wherein and the portable patient monitor and the therapy applicator are configured to establish an optical data link responsive to the portable patient monitor being docked to the therapy applicator.

15. The modular medical system of claim 1, wherein the portable patient monitor is further configured to be docked to at least one additional medical device.

* * * * *